(12) United States Patent
Melde et al.

(10) Patent No.: US 11,262,699 B2
(45) Date of Patent: Mar. 1, 2022

(54) APPARATUS AND METHOD FOR CREATING A HOLOGRAPHIC ULTRASOUND FIELD IN AN OBJECT

(71) Applicants: MAX-PLANCK-GESELLSCHAFT ZUR FOERDERUNG DER WISSENSCHAFTEN E.V, Munich (DE); FRAUNHOFER-GESELLSCHAFT ZUR FOERDERUNG DER ANGEWANDTEN FORSCHUNG E.V., Munich (DE)

(72) Inventors: Kai Melde, Stuttgart (DE); Peer Fischer, Freiburg (DE); Peter-Karl Weber, Saarbruecken (DE)

(73) Assignees: MAX-PLANCK-GESELLSCHAFT ZUR FOERDERUNG DER WISSENSCHAFTEN E.V., Munich (DE); FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 352 days.

(21) Appl. No.: 15/778,409

(22) PCT Filed: Dec. 7, 2016

(86) PCT No.: PCT/EP2016/002062
§ 371 (c)(1),
(2) Date: May 23, 2018

(87) PCT Pub. No.: WO2017/097417
PCT Pub. Date: Jun. 15, 2017

(65) Prior Publication Data
US 2018/0341221 A1 Nov. 29, 2018

(30) Foreign Application Priority Data
Dec. 11, 2015 (EP) ..................... 15003540

(51) Int. Cl.
*G03H 1/08* (2006.01)
*A61B 90/98* (2016.01)
(Continued)

(52) U.S. Cl.
CPC ........... *G03H 1/0891* (2013.01); *A61B 90/98* (2016.02); *A61N 7/02* (2013.01); *G01N 29/0663* (2013.01);
(Continued)

(58) Field of Classification Search
CPC ... A61B 17/22012; A61B 90/90; A61B 90/98; A61N 2007/0056; A61N 2007/006;
(Continued)

(56) References Cited

U.S. PATENT DOCUMENTS 4,977,601 A 12/1990 Bicz
5,212,571 A * 5/1993 Garlick .................... G03H 3/00
359/9

(Continued)

FOREIGN PATENT DOCUMENTS

CN 101317138 A 12/2008
CN 102089634 A 6/2011
(Continued)

OTHER PUBLICATIONS

Fleury et al. (2010) High intensity therapeutic ultrasound transducer performance and characterisation. International Ultrasonics Symposium Proceedings IEEE, p. 876-85.
(Continued)

*Primary Examiner* — Pascal M Bui Pho
*Assistant Examiner* — Alexei Bykhovski
(74) *Attorney, Agent, or Firm* — Caesar Rivise, PC (57) ABSTRACT

An ultrasonic apparatus (100) for creating a holographic ultrasound field (1) comprises an ultrasound source device (10) being adapted for creating an ultrasound wave, and a transmission hologram device (20) having a transmission hologram (21) and an exposed acoustic emitter surface (22), said transmission hologram device (20) being acoustically coupled with the ultrasound source device (10) and being arranged for transmitting the ultrasound wave through the acoustic emitter surface (22) and creating the holographic
(Continued)

ultrasound field in a surrounding space, wherein the acoustic emitter surface (22) is a smooth surface which do not influence the field distribution of the ultrasound wave. Furthermore, a method of creating a holographic ultrasound field in an object (3), wherein the ultrasonic apparatus (100) is used, and applications of the ultrasonic apparatus (100) are described.

15 Claims, 3 Drawing Sheets (51) Int. Cl.
| | | |
|---|---|---|
| *G01N 29/06* | (2006.01) | |
| *G02B 5/32* | (2006.01) | |
| *G03H 3/00* | (2006.01) | |
| *G01N 29/24* | (2006.01) | |
| *G03H 1/02* | (2006.01) | |
| *A61N 7/02* | (2006.01) | |
| *A61N 7/00* | (2006.01) | |
| *A61B 90/90* | (2016.01) | |
| *G03H 1/00* | (2006.01) | |
| *G03H 1/04* | (2006.01) | |
| *G03H 1/22* | (2006.01) | |
| *A61B 17/22* | (2006.01) | |

(52) U.S. Cl.
CPC .......... *G01N 29/2418* (2013.01); *G02B 5/32* (2013.01); *G03H 1/0244* (2013.01); *G03H 3/00* (2013.01); *A61B 17/22012* (2013.01); *A61B 90/90* (2016.02); *A61N 7/022* (2013.01); *A61N 2007/006* (2013.01); *A61N 2007/0056* (2013.01); *A61N 2007/0078* (2013.01); *G03H 1/0256* (2013.01); *G03H 1/0476* (2013.01); *G03H 2001/0077* (2013.01); *G03H 2001/0094* (2013.01); *G03H 2001/0484* (2013.01); *G03H 2001/0816* (2013.01); *G03H 2001/2234* (2013.01); *G03H 2210/36* (2013.01); *G03H 2210/63* (2013.01); *G03H 2223/25* (2013.01); *G03H 2227/02* (2013.01); *G03H 2227/06* (2013.01)

(58) Field of Classification Search
CPC .. A61N 2007/0078; A61N 7/02; A61N 7/022; G01N 29/0663; G01N 29/2418; G02B 5/32; G03H 1/0244; G03H 1/0256; G03H 1/0476; G03H 1/0891; G03H 2001/0077; G03H 2001/0094; G03H 2001/0484; G03H 2001/0816; G03H 2001/2234; G03H 2210/36; G03H 2210/63; G03H 2223/25; G03H 2227/02; G03H 2227/06; G03H 3/00

See application file for complete search history.

(56) References Cited

U.S. PATENT DOCUMENTS

| | | | |
|---|---|---|---|
| 6,729,337 | B2 | 5/2004 | Dawson |
| 8,696,164 | B2 | 4/2014 | Kalms et al. |
| 8,848,481 | B2 | 9/2014 | Hald |
| 10,025,272 | B2 | 7/2018 | Falter et al. |
| 2003/0145864 | A1 | 8/2003 | Dawson |
| 2004/0129088 | A1* | 7/2004 | Moscaritolo ............ G01F 1/667 73/861.25 |
| 2005/0277824 | A1 | 12/2005 | Aubry et al. |
| 2014/0118807 | A1 | 5/2014 | Su |
| 2016/0213315 | A1* | 7/2016 | Hyde .................. A61B 5/0507 |
| 2017/0348907 | A1 | 12/2017 | Melde et al. |

FOREIGN PATENT DOCUMENTS

| | | |
|---|---|---|
| CN | 102262301 A | 11/2011 |
| CN | 103961142 A | 8/2014 |
| EP | 3034281 A1 | 6/2016 |
| JP | 62-277971 A | 12/1987 |
| JP | 63503206 A | 11/1988 |
| JP | 06-194348 A | 7/1994 |
| WO | 2006055470 A1 | 5/2006 |
| WO | 2007044002 A1 | 4/2007 |
| WO | 2013108152 A1 | 7/2013 |

OTHER PUBLICATIONS

Her Izberg et al. (2011) Bypassing absorbing objects in focused ultrasound using computer generated holographic technique. Med. Phys., 38(12), p. 6407-15.
Meyer et al. (2004). Binary optoacoustic holography with a spatial light modulator Journal of Applied Physics, 96(10) p. 5886-91.
Moleron et al. (2014). Acoustic fresnel lenses with extraordinary transmission. Applied Physics Letters, 105, p. 1-5.
English Translation of Chinese Office Action dated Mar. 26, 2020.
English Translation of Chinese Search Report dated Mar. 26, 2020.
Machine Translation of JP 62-277971 A (1987).
English Abstract for JP 06-194348 A (1994).
Japanese Office Action and Translation dated Jul. 9, 2020.
Chinese Office Action and Translation dated Dec. 7, 2020.

* cited by examiner

APPARATUS AND METHOD FOR CREATING A HOLOGRAPHIC ULTRASOUND FIELD IN AN OBJECT

CROSS-REFERENCE TO RELATED APPLICATIONS

This application is a U.S. National Phase Application of PCT/EP2016/002062, filed Dec. 7, 2016, which claims priority from EP 15003540.0, filed Dec. 11, 2015, the contents of which applications are incorporated herein by reference in their entireties for all purposes.

BACKGROUND OF THE INVENTION

The present invention relates to an ultrasonic apparatus being configured for creating a holographic ultrasound field in an object. Furthermore, the invention relates to a method of creating a holographic ultrasound field in an object. Applications of the invention are available in the fields of treating objects with ultrasound, ultrasound-based energy transmission and/or ultrasound imaging, in particular in medical engineering.

For describing the background of the invention, particular reference is made to the following citations:
[1] A. Meyer et al. in "Journal of Applied Physics" 96(10): 5886-5891 (2004);
[2] U.S. Pat. No. 8,696,164 B2;
[3] M. Molerón et al. in "Applied Physics Letters" 105(11): 114109 (2014);
[4] Y. Hertzberg et al. in "Medical Physics" 38(12): 6407-6415 (2011);
[5] WO 2013/108152 A1;
[6] US 2003/145864 A1;
[7] G. Fleury et al. in "Ultrasonics symposium (IUS)", 2010 IEEE, 11 Oct. 2010, pages 876-885;
[8] US 2005/277824 A1; and
[9] European patent application No. 14004333.2 (not published on the priority date of the present specification).

Employing ultrasound for contact-free energy transmission to a target section in an object is generally known in various processes in medical engineering (e. g. ultrasound-based thermal therapy or surgery) and industrial techniques. Usually, ultrasound fields having a spatial structure are required for an efficient irradiation of the target section, which can be locally limited or variable. Practical approaches use movable sound transmitters with a fixed point or line shaped focus or phased-array sources with a controllable focal point. Movable sound transmitters have disadvantages in terms of a precise and reproducible adjustment relative to the object. In a phased-array source, each pixel is a separate sound transmitter requiring a specific electronic control. This results in strongly increasing complexity (in particular costs, size, software requirements) with increasing number of pixels, which typically is e.g. 128 or 256.

Spatially structured ultrasound fields can be obtained by opto-acoustic holography as described by Meyer et al. [1], wherein a strong laser source is used for exciting single spots of an optically absorbing surface. Another device for laser-optical generation of mechanical waves is described in [2]. While these methods provide a high local resolution and dynamic acoustic fields, they have disadvantages in terms of complexity and restricted efficiency resulting from the complex optical set-up. Furthermore, the method of [1] is not suitable for a continuous operation, and a high laser intensity is required even for creating a low ultrasound pressure, which is limited to 8 kPa per single spot.

M. Molerón et al. [3] describe a Fresnel sound lens having extraordinary sound transmission using features that are smaller than the wavelength. The application of the Fresnel sound lens is restricted to focussing sound waves to a single focal spot. Y. Hertzberg et al. [4, 5] have suggested to use acoustic holograms for bypassing absorbing objects in focused ultrasound for medical applications. The acoustic holograms are created with a phased-array source having 986 pixels. This large number of pixels causes a high complexity of the electronic control and a restriction of the adjustability of the phase per pixel to $\pi/4$ steps.

An ultrasonic apparatus creating a holographic ultrasound field by using a combination of ultrasonic transducers is disclosed in [6]. This technique has disadvantages in terms of complexity as one emitter is needed per each image element (pixel) and all emitters within an array have to be individually controlled. Further background of creating ultrasound fields can be found in [7] and [8].

Another application of spatially structured ultrasound fields is available in the field of 3D rapid prototyping [9]. A holographic ultrasound field generated with a transmission hologram is used for applying acoustic forces on a precursor material in a liquid bath. The resulting material distribution is subjected to a fixation process. The technique of [9] is adapted for the creation of the holographic ultrasound field within the liquid bath.

OBJECTS OF THE INVENTION

Objectives of the invention are to provide an improved ultrasonic apparatus and an improved method for creating spatially structured ultrasound fields, wherein disadvantages and limitations of conventional techniques are avoided. In particular, the ultrasonic apparatus and the method are to be capable to provide further practical applications of spatially structured ultrasound fields and to create a holographic ultrasound field with reduced device and control complexity.

BRIEF SUMMARY OF THE INVENTION

According to a first general aspect of the invention, the above objective is solved by an ultrasonic apparatus, which is configured for creating at least one holographic ultrasound field and which comprises an ultrasound source device for generating a primary ultrasound wave and a transmission hologram device being arranged in acoustic contact with the ultrasound source device so that the primary ultrasound wave can propagate through the transmission hologram device, thus creating a secondary ultrasound wave, which forms the at least one holographic ultrasound field in a surrounding space, e.g. in an adjacent object. The ultrasound source device includes at least one ultrasound source element (transducer element), which is capable of emitting the primary ultrasound wave in response to a driving signal (driving current). The transmission hologram device includes a transmission hologram and an exposed acoustic emitter surface facing to the surrounding. Preferably, the transmission hologram is a structured, stable component, providing a passive, static modification of the primary ultrasound wave. Advantageously, this enables the full acoustic intensity to be provided by the primary ultrasound source device. Further, it enables highly defined ultrasound fields without the complexity of phased array sources. A transmission hologram's complexity is limited by the fabrication method only. Once it is made, a 100×100 pixel hologram does not require less or more control than a hologram measuring 500×500 pixels.

According to the invention, the acoustic emitter surface of the ultrasonic apparatus is a smooth surface. Depending on the shape of the wave-front of the secondary ultrasound wave and/or the geometry of the surface of the object to be treated, the acoustic emitter surface is a plane or curved surface. The term "smooth surface" refers to an outer non-structured surface (step-free surface), in particular a surface, which is capable of transmitting the ultrasound without changing the radial phase and/or amplitude distribution of the ultrasound. In other words, the term "smooth surface" is not necessarily an ideally step-free surface, but may include topographic features, which do not influence the radial field distribution of the ultrasound (or influence it in a negligible way only). This is in contrast with the holographic surface, which is not a smooth surface. Generally, the surface roughness of the acoustic emitter surface is reduced such that voids (e. g. air or impurity pockets) are minimized or excluded at the interface between the ultrasonic apparatus and an adjacent object.

Compared with the conventional techniques, the ultrasonic apparatus has the following substantial advantages. Firstly, the complexity of controlling a phased array of ultrasound source elements as mentioned in [4, 5, 6, 8] is avoided. Furthermore, contrary to [3], the application of a transmission hologram instead of a focussing sound lens offers new applications of the ultrasonic apparatus as the transmission hologram is capable to form the holographic ultrasound field, e.g. in the object to be irradiated, with any specific field distribution to be applied in the ultrasound frequency range.

Furthermore, the smooth acoustic emitter surface enables the application of the ultrasonic apparatus in practical environments, e.g. by a physician for applying the holographic ultrasound field to a patient. Advantageously, the acoustic emitter surface allows to overcome the need of the conventional devices, e. g. according to [3] or [6], to be operated in a liquid bath. The acoustic emitter surface provides a direct, distortion-free contact with the surface of an object to be treated. Furthermore, the smooth topography of the emitter surface avoids the adherence of contaminations, which could deteriorate the holographic ultrasound field, and facilitates any cleaning operation. If the ultrasonic apparatus is to be used with an additional sound coupling layer, e.g. with a gel layer as known from conventional ultrasound applications, the creation of any unintended air bubbles at the acoustic emitter surface is avoided.

According to the invention, the transmission hologram is used to structure acoustic fields in a simple and cost-efficient way. Such holograms offer wave-front manipulation over large areas (up to tens of centimeters) with high resolution, e.g. at least 512×512 "pixels". Arbitrary pressure distributions can thus be generated even using one single piezoelectric transducer. The holograms are much simpler, cheaper, and easier to operate compared with complex transducer arrays.

According to a second general aspect of the invention, the above objective is solved by a method of creating a holographic ultrasound field in an object, wherein the ultrasonic apparatus according to the above first aspect of the invention is used. The ultrasonic apparatus is arranged in acoustic contact (sonic contact) with the object and operated such that the holographic ultrasound field is created in the object. The holographic ultrasound field is created according to the acoustic phase and/or amplitude structure of the transmission hologram.

Advantageously, the ultrasound source device of the ultrasonic apparatus may include at least one ultrasound source element, e.g. at least one piezoelectric element, as it is known from conventional ultrasonic applications. According to preferred embodiments of the invention, the ultrasound source device comprises at least one of one single ultrasound source element and an array of ultrasound source elements, in particular a phased array of ultrasound source elements. According to a first variant, the single ultrasound source element can be used for creating the primary ultrasound wave, which propagates through the transmission hologram. Using the single ultrasound source element has advantages in terms of a simple device structure and a simple control of the ultrasound source device. According to a second variant, the array of ultrasound source elements (at least two ultrasound source elements) is provided. This can have advantages for additionally shaping the primary ultrasound wave and the holographic ultrasound field to be created, while the limitations of high resolution arrays and the control thereof are avoided. According to a third variant, both of a single ultrasound source element and an array of ultrasound source elements can be provided. Due to the known features of the at least one ultrasound source element and the control thereof, the primary ultrasound wave has a pre-known wave-front. Preferably, the primary ultrasound wave has a frequency in a non-audible frequency range, in particular ultrasound frequency range. Particularly preferred, the acoustic waves have a frequency of at least 20 kHz, in particular at least 40 kHz, up to the GHz-range.

Preferably, the ultrasound source device is adapted for creating the primary ultrasound wave such that it is a plane ultrasound wave (including a plane wave or a wave approximated to a plane wave). With this embodiment, the primary ultrasound wave initially emitted by the ultrasound source device has a homogeneous radial phase distribution (phase distribution perpendicular to the beam propagation direction). Advantageously, this facilitates the design of the transmission hologram. The plane primary ultrasound wave preferably is a continuous wave.

Alternatively, the ultrasound source device can be adapted for creating the ultrasound wave such that it is a curved, in particular paraboloid or spherical, ultrasound wave. With this embodiment, advantages for focussing the holographic ultrasound field can be obtained. The paraboloid or spherical primary ultrasound wave preferably is a pulse-shaped wave, e. g. consisting of one single acoustic oscillation or a group of acoustic oscillations.

However, the invention is not restricted to the use of plane, paraboloid or spherical waves. If other shapes of the wave-front initially generated by the ultrasound source device are used, the structure of the transmission hologram can be adapted accordingly.

According to a further preferred feature of the ultrasonic apparatus, the transmission hologram device, particularly preferred the transmission hologram thereof, has a planar outer shape. This facilitates the design of the transmission hologram and the creation of the holographic ultrasound field with high reproducibility and precision. The planar transmission hologram preferably is provided if the ultrasound source device, e. g. including at least one plane ultrasound source element, is adapted for creating the plane ultrasound wave. Preferably, the transmission hologram device with the planar transmission hologram has a plane acoustic emitter surface.

Alternatively, the transmission hologram device, particularly preferred the transmission hologram thereof, has a curved, in particular paraboloid or spherical outer shape.

This embodiment preferably is provided if the ultrasound source device is adapted for creating the curved, in particular paraboloid or spherical ultrasound wave. With this case, the ultrasound source device includes at least one curved ultrasound source element or multiple plane ultrasound source elements arranged along a curved surface. Preferably, the transmission hologram device with the curved transmission hologram has a curved acoustic emitter surface with a curvature matched to the curvature of the transmission hologram.

Additionally, the shape of the acoustic emitter surface can be matched to the geometry of the surface of the object to be treated. In particular, the planar transmission hologram can be combined with a curved acoustic emitter surface, or a curved transmission hologram can be combined with a planar acoustic emitter surface.

The transmission hologram is a structured component which is capable of an interaction with the pre-known wave-front of the primary ultrasound wave such that the phases and/or amplitudes across the wave-front are specifically changed by the structure of the transmission hologram. To this end, the transmission hologram has a hologram phase structure extending perpendicular (in radial directions) relative to the propagation direction of the primary ultrasound wave (axial direction). Each changed phase and/or amplitude provides a sub-wave contribution for a subsequent diffraction of the secondary ultrasound wave. The acoustic sub-waves interfering with each other are created by the transmission hologram. Thus, the transmission hologram is used like a holographic plate in optical holography or a diffractive optical element in projection optics. After the interaction of the wave-front of the primary ultrasound wave with the transmission hologram, the holographic ultrasound field to be obtained is generated by diffraction and self-interference of the secondary ultrasound wave, i.e. by interference of the sub-waves in at least one focal plane in the adjacent object. The self-interference creates the intensity distribution of the holographic ultrasound field to be obtained.

The transmission hologram is made of a material with an acoustic impedance, which differs from the acoustic impedance of the surrounding materials. Thus, the hologram phase structure of the transmission hologram applies the phase and/or amplitude shifts to the primary ultrasound wave along the radial distribution thereof. Preferably, the transmission hologram is formed by a plastic material, like e. g. polymethylmethacrylate (PMMA), polystyrene (PS), a more ductile polymer such as polymethylpentene (PMP), an epoxy resin or silicone rubbers. PS, PMMA have low attenuation while PMP has an acoustic impedance that is better matched to biological tissue. The acoustic impedance of epoxies and silicones can be adjusted over a wide range using filler particles.

The transmission hologram is formed (structured and/or shaped) such that it matches the wave-front shape of the primary ultrasound wave and the holographic ultrasound field to be obtained. Advantageously, various embodiments of the invention are available for forming the transmission hologram, in particular for obtaining structure data for forming the hologram phase structure. According to a first variant, the structure data can be formed obtained by solving the inverse diffraction problem in dependency on the holographic ultrasound field to be created and the radial phase and amplitude distribution of the primary ultrasound wave. According to a second variant, the transmission hologram can be formed as a phase hologram formed by a numerical approximation using an error-reduction algorithm, such as the Gerchberg-Saxton algorithm or the iterative angular spectrum approach, in dependency on the holographic ultrasound field to be created and the radial phase and amplitude distribution of the primary ultrasound wave. The error-reduction algorithm can be applied as it is known from optics, and the calculation can readily be adapted to acoustics.

Advantageously, the transmission hologram can be made using the calculated hologram phase structure by the use of a rapid prototyping method, e. g. a 3D printing method. This has advantages in terms of high resolution (e. g. 50 μm), high-speed and cheap manufacturing, and capability of digital material combinations.

The hologram phase structure of the transmission hologram preferably is determined by the shape of a holographic surface thereof, e. g. the interface between the transmission hologram material and an embedding material. For example, a hologram phase structure follows from a variable thickness of the transmission hologram, $\Delta\Phi(r)=2\pi f(1/c_m-1/c_h)\Delta T(r)$, where $\Delta\Phi$ is the radial phase shift, $\Delta T$ the relative thickness difference, f the frequency, r the coordinate in the radial direction and $c_m$, $c_h$ the speed of sound in embedding material and transmission hologram, respectively. According to a preferred embodiment of the invention, the transmission hologram is arranged such that the holographic surface faces to the acoustic emitter surface. With this embodiment, the transmission hologram device includes a sonic coupling layer, which is arranged on the holographic surface of the transmission hologram and which provides the acoustic emitter surface. The sonic coupling layer is fixedly coupled with the holographic surface, so that the hologram phase structure of the holographic surface is protected against influences from the environment. Furthermore, the sonic coupling layer provides the smooth and gap-free contact with the object to be irradiated.

Particularly preferred, the sonic coupling layer comprises an embedding material covering the holographic surface. The embedding material has an acoustic impedance differing from the acoustic impedance of the transmission hologram. The embedding material has advantages for obtaining the hologram phase structure, and matching the impedance to the object to be treated. The acoustic emitter surface is a smooth surface, as opposed to the variable surface of the transmission hologram.

Further preferred, the transmission hologram is a solid component, while the embedding material of the sonic coupling layer may consist of a solid or liquid, including gel-like, substance. With preferred examples, the embedding material comprises a non-volatile, non-toxic solvent, such as glycerine, or an ultrasound gel, e. g. including a mixture of glycerine and propylene glycol. Preferably, the acoustic impedance of the embedding material is matched to the acoustic impedance of the object to be treated.

According to a further preferred feature of the invention, the sonic coupling layer can comprise a cover sheet covering the embedding material and providing the acoustic emitter surface. Advantageously, the cover sheet provides an enclosure in particular for a flowable, e. g. gel-like, embedding material. Advantageously, the cover sheet can be flexible to adjust to contours of the object to be treated.

The transmission hologram device can be fixedly coupled with the ultrasound source device. With this embodiment, advantages in terms of a fixed axial orientation of the transmission hologram relative to the ultrasound source device and the sonic coupling of the transmission hologram with the ultrasound source device are obtained.

Alternatively, according to a particularly preferred modification of the invention, the transmission hologram device is detachably coupled with the ultrasonic source device, so that advantages for adapting the ultrasonic apparatus to a particular application task can be obtained. The transmission hologram device is provided as an exchangeable component. In particular, the transmission hologram device can be adapted for a particular irradiation function and/or a particular object to be irradiated. With a particularly preferred example, the transmission hologram device can be personalized, i.e. the hologram phase structure of the transmission hologram can be configured in dependency on the requirements for irradiating a particular individual, like e.g. a patient.

Preferably, the transmission hologram device is provided with at least one identification device, so that advantages are obtained in particular for the use of detachably coupled transmission hologram devices. The at least one identification device preferably includes at least one of an optically readable marker, like e. g. a text information or an optically readable code, and an electronic identification unit, like e.g. an RFID transducer. Advantageously, mistakes in using the appropriate transmission hologram device are avoided by the at least one identification device.

The transmission hologram is formed on the basis of a specific ultrasound input, e. g. the characteristic wave-front of primary ultrasound wave created with the ultrasound source device. Accordingly, it is desired that the transmission hologram has an appropriate orientation, in particular appropriate rotation around the beam axis, i. e. axial orientation relative to the propagation direction of the primary ultrasound wave. Additionally, if the ultrasonic apparatus has the function of projecting a specific holographic image or beam trajectory into the object, the orientation of the transmission hologram (rotation around the beam axis) will be important as well. Furthermore, if the acoustic emitter surface, and in particular the sonic coupling layer, is optically transparent, the hologram surface of the transmission hologram looks random to a human user. This makes it difficult to find the appropriate orientation by considering the transmission hologram. Therefore, according to yet another advantageous embodiment of the invention, at least one of the ultrasound source device and the transmission hologram device is provided with at least one alignment element. The alignment element comprises at least one of a visible mark and a geometric structure allowing an appropriate geometric orientation of the transmission hologram device relative to the ultrasound source device. Advantageously, the alignment element improves the precision and reproducibility of creating the holographic ultrasound field. Furthermore, the at least one alignment element allows to support the correct orientation of the transmission hologram device relative to the ultrasound source device and/or the object to be irradiated.

Preferably, the at least one alignment element is configured such that the transmission hologram device can only be mounted correctly to the ultrasound source device. With a preferred example, the at least one alignment element comprises a protruding structure, like e.g. a pin, preferably arranged in an edge section of the transmission hologram device outside the transmission hologram.

According to a further preferred embodiment of the invention, the ultrasonic apparatus is provided with a power source device and a waveform generator. The power source device is adapted for supplying the driving current to the ultrasound source device. The power source device is controlled by the waveform generator, which is adapted for controlling an amplitude waveform of the driving current. According to advantageous embodiments of the invention, the waveform generator and the power source device are adapted for driving the ultrasound source device such that the primary ultrasound wave is a continuous wave or a pulsed wave.

Contrary to the conventional techniques, the ultrasonic apparatus of the invention preferably is adapted for an application outside a liquid bath, e. g. in a gaseous, in particular atmospheric environment. Therefore, according to a further embodiment of the invention, the ultrasonic apparatus preferably is provided with a support device, which is coupled with the ultrasound source device. According to the preferred applications of the invention, the support device comprises at least one of a handle, a probe head and an endoscope device.

A further advantage of the invention is obtained by the plurality of applications of the holographic ultrasound field created in the object to be irradiated. According to a first example, the holographic ultrasound field is adapted for creating at least one ultrasound focus in the object. According to an alternative example, at least one ultrasound image can be created in the object, e.g. for irradiating or moving a foreign subject in the object. As the holographic ultrasound field is created with a distance from the ultrasonic apparatus, the transmission hologram can be configured such that a predetermined range within the object can be bypassed by the ultrasound, in particular the holographic ultrasound field to be created.

Furthermore, the holographic ultrasound field can be used for ultrasound imaging the object and/or an ultrasound-based energy transmission into the object.

Preferred medical applications of the invention are available in the fields of pain treatment, high intensity focussed ultrasonic therapy, treatment of biological tissue and/or destroying kidney or bladder stones.

BRIEF DESCRIPTION OF SEVERAL VIEWS OF THE DRAWINGS

Further details and advantages of the invention are described in the following with reference to the attached drawings, which show in.

DETAILED DESCRIPTION OF PREFERRED EMBODIMENTS

Preferred embodiments of the invention are described in the following with exemplary reference to an ultrasonic apparatus being adapted for medical applications. It is emphasized that the application of the invention is not restricted to the medical applications, but rather can be used for other applications as well, like in the field of material processing or non-destructive investigation of materials. Furthermore, reference is made to embodiments of the ultrasonic apparatus, wherein the ultrasound source device includes one single plane ultrasound source element and the transmission hologram has a planar shape. The invention can be implemented with a curved ultrasound source element, a plane or curved array of ultrasound source elements and/or a transmission hologram having a curved shape in a corresponding manner.

The drawings represent schematic illustrations only. In a practical implementation, power supply and control units are provided for operating the ultrasound source device. In particular, control units are provided for applying operation voltages to oscillators of acoustic sources, thus defining the amplitude, frequency and phase of the primary acoustic waves emitted by the ultrasound source device.

Figure 1:
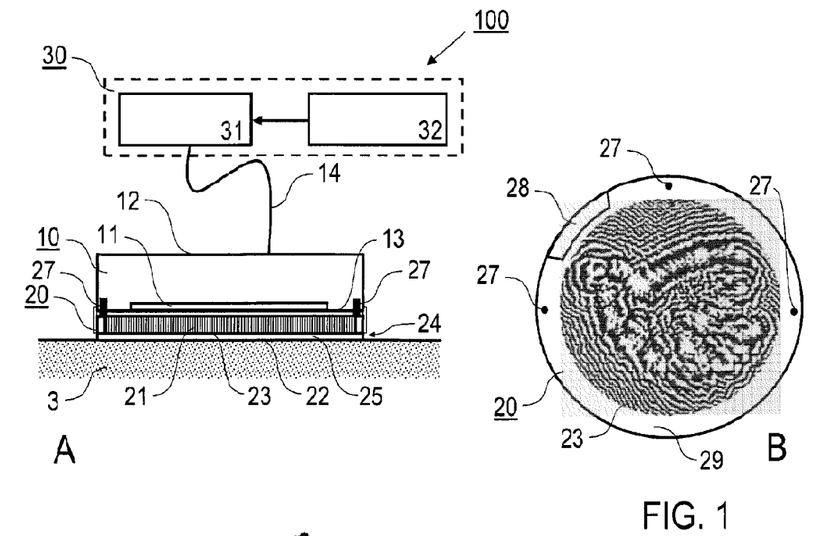
FIG. 1: a schematic illustration of an embodiment of the inventive ultrasonic apparatus.

According to FIG. 1, a first embodiment of the ultrasonic apparatus 100 of the invention comprises an ultrasound source device 10, a transmission hologram device 20 and a control device 30. FIG. 1A shows these components as a schematic cross-sectional illustration, while FIG. 1B shows a plane view of the exposed emitter side of the transmission hologram device 20.

The ultrasound source device 10 comprises a single ultrasound source element 11, which is arranged in a casing 12 on a carrier plate 13. With the embodiment of FIG. 1, the carrier plate 13 is a side wall of the casing 12. The single ultrasound element 11 is in sonic contact with the carrier plate 13, e.g. via a glue connection layer. The ultrasound source device 10 is provided with a connecting cable 14, which couples the control device 30 with the single ultrasound source element 11. The single ultrasound source element 11 is e.g. a piezoelectric plate, in particular the commercially available transducer plate made of PZT-8, e.g. with a diameter of 50 mm and a thickness of 1 mm.

Figures 3, 4:
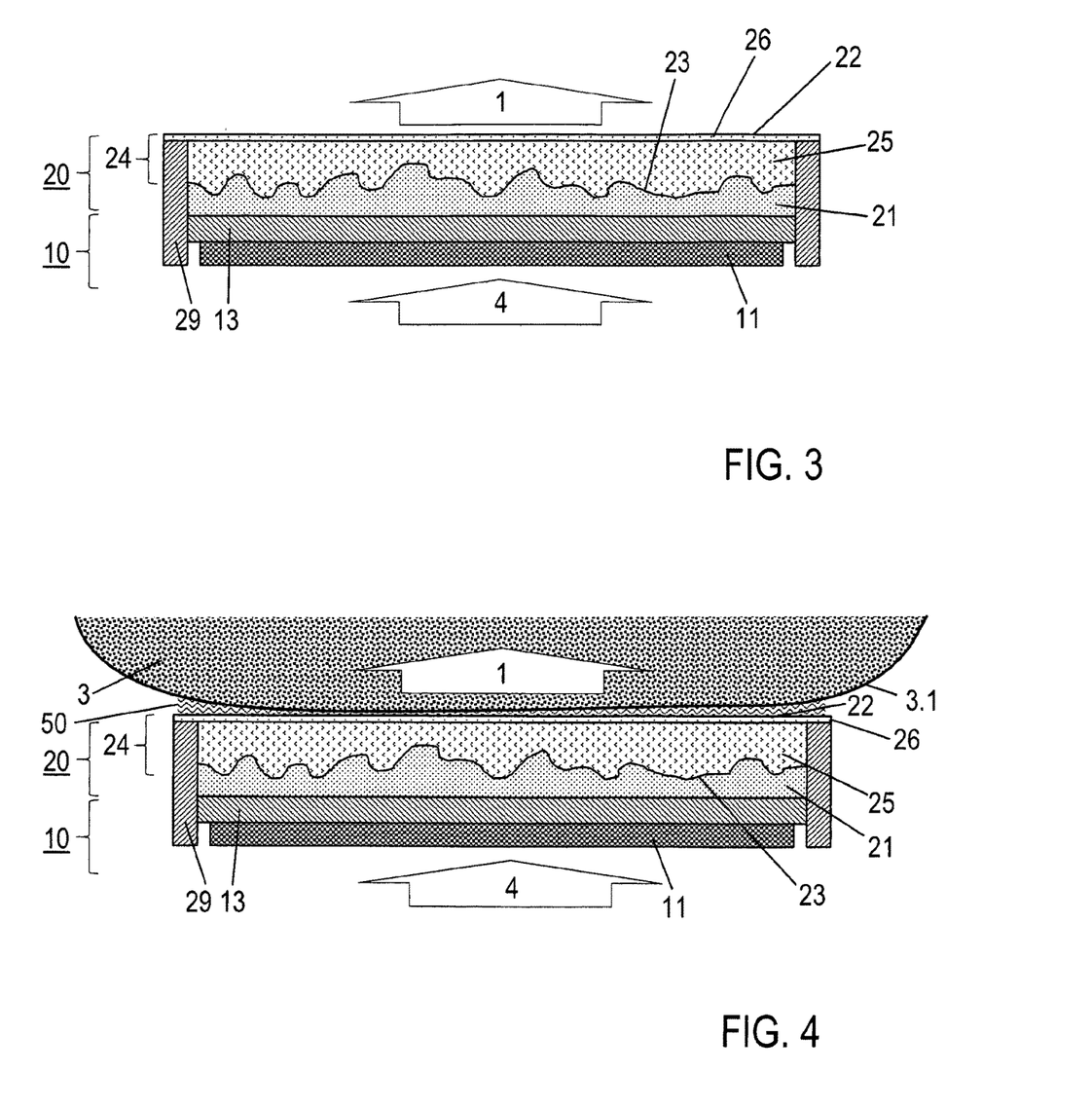
FIGS. 3, 4: cross-sectional views of an ultrasonic apparatus according to further embodiments of the invention.

The transmission hologram device 20 comprises a transmission hologram 21, wherein a first continuous substrate side of the transmission hologram 21 is in sonic contact with the carrier plate 13 and a second, opposite side of the transmission hologram 21, having a structured holographic surface 23, faces away from the ultrasound source device 10 (see further details in FIGS. 3 and 4). The transmission hologram 21 is made of e.g. PMMA. For improving the sonic contact between the carrier plate 13 and the transmission hologram 21, another sonic coupling layer, e.g. made of a gel, can be provided there between.

According to the invention, the holographic surface 23 is not exposed to the surrounding, but covered by a sonic coupling layer 24, which provides an exposed acoustic emitter surface 22 of the transmission hologram device 20. The sonic coupling layer 24 is formed by a single layer of an embedding material 25 which completely covers the holographic surface 23 and which has a smooth acoustic emitter surface 22 opposite to the holographic surface 23. The embedding material 25 is made of a substance having a different acoustic impedance compared with the transmission hologram 21, e.g. glycerine or silicone.

With a transparent sonic coupling layer 24, the plan view of the acoustic emitter surface 22 (FIG. 1B) shows the holographic surface 23 surrounded by an edge 29. Alignment elements 27 and an identification device 28 are provided at the edge 29. The alignment elements 27 comprise three pins protruding on the backside opposite to the acoustic emitter side and matching to three receptacles in the casing 12 of the ultrasound source device 10. Simultaneously, the pins provide connectors for a detachable connection of the transmission hologram device 20 with the ultrasound source device 10.

The control device 30 comprises a power source device 31, which is adapted for creating the driving current to be supplied to the single ultrasound source element 11 via the connection cable 14. Furthermore, the control device 30 comprises a waveform generator 32, which controls an amplitude waveform of the driving current such that a primary ultrasound wave 2 (see FIG. 2) created with the single ultrasound source element 11 has e.g. a continuous or pulse-shaped temporal characteristic.

The shape and size of the ultrasonic apparatus 100, in particular the components 10 and 20, are selected in dependency on the particular application thereof. With preferred applications in medicine, the components 10, 20 have e.g. a cylindrical shape with a circular acoustic emitter surface 22, having a diameter of e.g. 1 cm to 10 cm.

Figure 2:
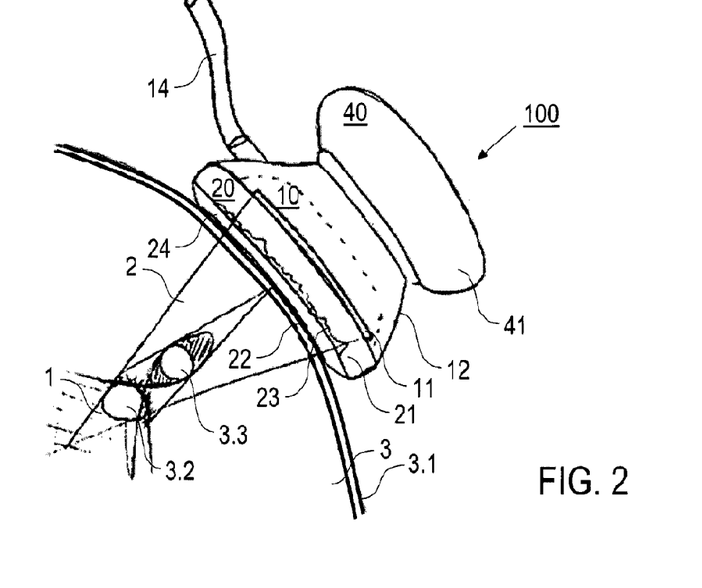
FIG. 2: an illustration of further details of an ultrasonic apparatus and the creation of the holographic ultrasound field.

FIG. 2 schematically illustrates a further embodiment of the ultrasonic apparatus 100, which is configured as a handheld device. The ultrasonic apparatus 100 is provided with a support device 40, which is connected with the ultrasound source device 10 and which comprises a handle 41. This embodiment of the invention is adapted for manual use, in order to create a holographic sound field 1 in an object 3, like e.g. the body of a patient to be irradiated.

The ultrasound source device 10 has a cone-shaped casing 12 accommodating the ultrasound source element 11 and being connected via the connection cable 14 with the control device (not shown). The transmission hologram device 20 is detachably coupled with the ultrasound source device 10. The transmission hologram 21 with the schematically illustrated holographic surface 23 is covered with the sonic coupling layer 24. The sonic coupling layer 24 provides the acoustic emitter surface 22, which is in direct contact with the outer surface 3.1 of the object, e.g. the outer skin of the patient. The ultrasonic apparatus 100 is adapted for use in the atmospheric environment of the object 3, e.g. in air.

The cross-sectional view of the object 3 in FIG. 2 illustrates an example of the invention, wherein the holographic sound field 1 is to be created in a target area 3.2 behind an obstacle 3.3. The primary ultrasound wave created with the ultrasound source element 11 is subjected to a phase and/or amplitude change by the transmission hologram 21. The transmission hologram 21 is designed such that the ultrasound propagating through the transmission hologram 21 has a low intensity area covering the obstacle 3.3, while the energy of the ultrasound wave is focussed to the target area 3.2. Accordingly, with medical applications, any organ in the obstacle area 3.3 can be protected, e.g. for the irradiation of prostate tissue in the target area 3.2.

With alternative embodiments of the invention, the support device 40 can be provided by another carrier selected in dependency on the application of the ultrasonic apparatus 100. With preferred examples, the ultrasonic apparatus can be integrated to an endoscopy device, in particular mounted at the distal end of an endoscope shaft. With a further example, the ultrasonic apparatus 100 can be arranged on a probe head, e.g. for ultrasound therapy of organs.

FIGS. 3 and 4 illustrate further preferred features of the invention with reference to the cross-sectional schematic illustration of the ultrasound source device 10 (partially shown) and the transmission hologram device 20.

The ultrasound source device 10 comprises a single ultrasound source element 11 being acoustically coupled with the carrier plate 13. The transmission hologram device 20 comprises the transmission hologram 21 with the holographic surface 23 and the sonic coupling layer 24, including an embedding material 25 and a cover sheet 26. The exposed surface of the cover sheet 26 provides the smooth acoustic emitter surface 22. The transmission hologram device 20 has an edge 29 portion for coupling with the ultrasound source device 10.

In response to the supply of the driving current 4 to the ultrasound source element 11, a primary ultrasound wave is emitted, which propagates through the transmission hologram 21. The radial distribution of the phases and/or amplitudes of the primary ultrasound wave are modified by the transmission hologram 21, in particular by the holographic surface 23, i.e. the interface between the material of the transmission hologram 21 and the embedding material 25. The holographic surface 23 is designed such that a predetermined holographic sound field 1 is created in the surrounding, e.g. in an object to be irradiated (see FIG. 4).

Preferably, the transmission hologram 21 is made of a solid material, like e.g. PMMA, while the embedding material 25 is a solid, e.g. silicone rubber, or liquid, e.g. glycerine, substance. Alternatively, the embedding material 25 can comprise a solid substance, and the transmission hologram 21 can comprise a liquid substance.

The cover sheet 26 is a membrane, which is made e.g. of silicone rubber. The membrane is a flexible, soft component, which provides a compliant surface and seals the transmission hologram 21 and the embedding material 25. Furthermore, the acoustic emitter surface 22 of the cover sheet 26 provides a bubble free, dirt free assembly and acoustic contact with the object 3.

For improving the acoustic contact with the object 3, a liquid coupling layer 50 can be provided between the outer surface 3.1 of the object 3 and the acoustic emitter surface 22. The liquid coupling layer 50 comprises e.g. an ultrasound gel.

Figure 5:
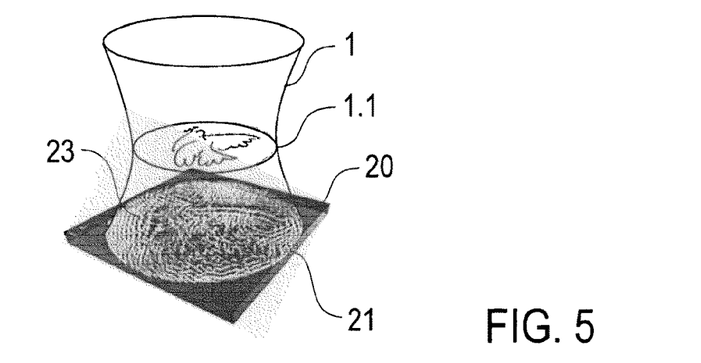
FIGS. 5 to 7: illustrations of the practical creation of a transmission hologram and a holographic ultrasound field.

FIG. 5 schematically illustrates the creation of the holographic sound field 1 with the transmission hologram 21 of the transmission hologram device 20. The holographic surface 23 of the transmission hologram 21 is designed such that a predetermined ultrasound image 1.1 is created in a focal plane of the transmission hologram 21. With alternative embodiments of the invention, the transmission hologram 21 can have multiple focal planes, so that equal or different ultrasound images can be created at different axial distances from the transmission hologram 21.

Figure 6:
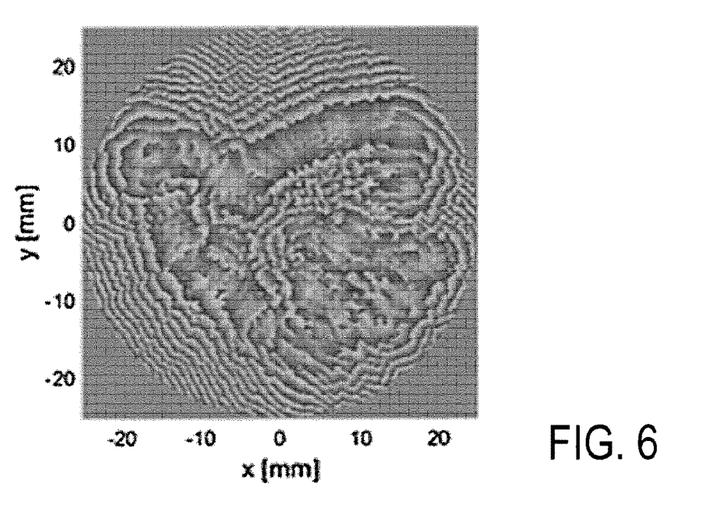

For creating the transmission hologram, the holographic ultrasound field to be created, e. g. the ultrasound image 1.1 in the focal plane, and the radial phase and amplitude distribution of the primary ultrasound wave, e. g. an approximated plane wave, are used as input for iteratively calculating a phase hologram. An error-reduction algorithm, such as the Gerchberg-Saxton algorithm, is used for calculating the phase hologram. FIG. 6 schematically illustrates the phase distribution of the transmission hologram 21 after the application of 20 iterations of the Gerchberg-Saxton algorithm. With each iteration, the propagation of the acoustic wave between the plane of the transmission hologram and the focal plane is modelled, wherein the pressure distribution in the focal plane is used as a boundary condition. The phase distribution is converted to a holographic surface depending on the material parameters of the transmission hologram 21 and the embedding material 25 (see e. g. FIG. 4). According to the calculated holographic surface, a transmission hologram with the hologram phase structure can be printed, e.g. with a 3D printing method.

Figure 7:
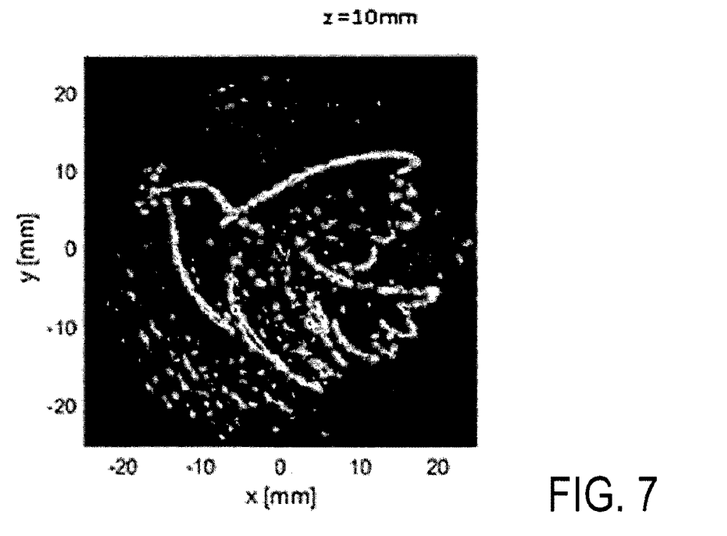

The printed transmission hologram is placed on the ultrasonic sound device as described above for creating the ultrasound image 1.1 (FIG. 5). As an example, FIG. 7 shows the measured distribution of the acoustic pressure in the focal plane with a distance of 1 cm from the transmission hologram. This distribution has been measured with a hydrophone. The electrical power of the ultrasound source element is about 1.5 W and the mean acoustic pressure is about 25 kPa.

Another application of the invention is the contact-free energy transmission to implant components, e.g. in the body of a patient. It is known that implant components move through the body, wherein even small changes of the distance from the body surface or the orientation relative to the body surface reduce the efficiency of the energy transmission. By adapting the holographic ultrasound field to the present location of the implant component, measured e.g. by ultrasound imaging, the efficiency of the energy transmission can be improved by a simple adaptation of the focal point to the current position and orientation of the implant component.

The features of the invention disclosed in the above description, the figures and the claims can be equally significant for realizing the invention in its different embodiments, either individually or in combination or in subcombination.

The invention claimed is:

1. An ultrasonic apparatus, being configured for creating a holographic ultrasound field, comprising
    an ultrasound source device being configured for creating an ultrasound wave, and
    a transmission hologram device having a transmission hologram and an outer acoustic emitter surface, said transmission hologram device being coupled with the ultrasound source device and being arranged for transmitting the ultrasound wave through the outer acoustic emitter surface and creating the holographic ultrasound field in a surrounding space, wherein
    the transmission hologram is a structured component which has a holographic surface facing to the outer acoustic emitter surface and a hologram phase structure being determined by a shape of the holographic surface and extending perpendicular relative to a propagation direction of the ultra-sound wave and being capable of an interaction with the wave-front of the ultrasound wave such that the phases and/or amplitudes across the wave-front are specifically changed by the structure of the transmission hologram and the holographic ultrasound field is generated by diffraction and self-interference of the ultrasound wave after the interaction,
    the holographic surface is covered by a sonic coupling layer comprising a flowable embedding material which has an acoustic impedance differing from the acoustic impedance of the transmission hologram,
    a flexible cover sheet covers the embedding material and provides the outer acoustic emitter surface, and
    the outer acoustic emitter surface is a smooth surface, which is capable of transmitting the ultrasound wave without changing the radial phase and/or amplitude distribution of the ultrasound wave.

2. The ultrasonic apparatus according to claim 1, wherein the ultrasound source device comprises at least one of a single ultrasound source element and an array of ultrasound source elements.

3. The ultrasonic apparatus according to claim 1, wherein the ultrasound source device is configured for creating a planar, paraboloid or spherical ultrasound wave.

4. The ultrasonic apparatus according to claim 1, wherein the transmission hologram has a planar, paraboloid or spherical shape.

5. The ultrasonic apparatus according to claim 1, wherein the transmission hologram is formed by solving an inverse diffraction problem in dependency on the holographic ultrasound field to be created.

6. The ultrasonic apparatus according to claim 1, wherein the transmission hologram is a phase hologram formed by numerical approximation using an error-reduction algorithm, in dependency on the holographic ultrasound field to be created.

7. The ultrasonic apparatus according to claim 1, wherein the transmission hologram device is detachably coupled with the ultrasound source device.

8. The ultrasonic apparatus according to claim 1, wherein the transmission hologram device is provided with at least one identification device selected from the group consisting of an optically readable marker and an electronic identification unit.

9. The ultrasonic apparatus according to claim 1, wherein at least one of the ultrasound source device and the transmission hologram device is provided with at least one alignment element.

10. The ultrasonic apparatus according to claim 1, further comprising
a power source device being arranged for supplying a driving current to the ultrasound source device, and
a waveform generator being coupled with the power source device and being arranged for controlling an amplitude waveform of the driving current.

11. The ultrasonic apparatus according to claim 10, wherein
the waveform generator and the power source device are configured for driving the ultrasound source device such that the ultrasound wave is a continuous wave or a pulsed wave.

12. The ultrasonic apparatus according to claim 1, further including
a support device carrying the ultrasound source device and comprising at least one of a handle, a probe head and an endoscope device.

13. The ultrasonic apparatus according to claim 1, wherein
the transmission hologram is a static component.

14. A method of creating a holographic ultrasound field in an object, wherein the ultrasonic apparatus according to claim 1 is used, comprising the steps of
arranging the ultrasonic apparatus in acoustic contact with the object, and
operating the ultrasonic apparatus such that the holographic ultrasound field is created in the object.

15. The method according to claim 14, wherein the holographic ultrasound field is shaped for at least one of the following applications:
creating an ultrasound focus in the object,
creating an ultrasound image in the object,
bypassing a range in the object by the ultrasound,
ultrasound imaging of the object,
at least one of medical applications, pain treatment, High Intensity Focussed Ultrasonic (HIFU) therapy, treatment of biological tissue, and destroying kidney or bladder stones, and
ultrasound-based energy transmission.

* * * * *